US012599510B2

(12) United States Patent
Majestic et al.

(10) Patent No.: US 12,599,510 B2
(45) Date of Patent: Apr. 14, 2026

(54) ABSORBENT ARTICLE WITH LEAK-PROOF CONTAINMENT FLAPS

(71) Applicant: Kimberly-Clark Worldwide, Inc., Neenah, WI (US)

(72) Inventors: Matthew X Majestic, Appleton, WI (US); Lynn Lynch, Sherwood, WI (US); Janet E. Collins, Hortonville, WI (US); Austin N. Pickett, Nashville, TN (US); Amanda L. Plump, Appleton, WI (US); Joseph J. Sina, De Pere, WI (US); Lori A. Roocks, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 74 days.

(21) Appl. No.: 17/923,937

(22) PCT Filed: Jun. 19, 2020

(86) PCT No.: PCT/US2020/038733
§ 371 (c)(1),
(2) Date: Nov. 8, 2022

(87) PCT Pub. No.: WO2021/257095
PCT Pub. Date: Dec. 23, 2021

(65) Prior Publication Data
US 2023/0172766 A1     Jun. 8, 2023

(51) Int. Cl.
| | |
|---|---|
| *A61F 13/15* | (2006.01) |
| *A61F 13/49* | (2006.01) |
| *A61F 13/494* | (2006.01) |
| *A61F 13/84* | (2006.01) |

(52) U.S. Cl.
CPC .. *A61F 13/49413* (2013.01); *A61F 13/49011* (2013.01); *A61F 2013/4948* (2013.01); *A61F 2013/8497* (2013.01)

(58) Field of Classification Search
CPC .......... A61F 13/49413; A61F 13/49011; A61F 2013/4948; A61F 2013/8497

USPC .......................... 604/385.31, 385.27, 385.28
See application file for complete search history.

(56) References Cited

U.S. PATENT DOCUMENTS

| | | | |
|---|---|---|---|
| 4,846,825 A * | 7/1989 | Enloe .................. | A61F 13/5633 604/385.22 |
| 5,593,401 A | 1/1997 | Sosalla et al. | |
| 7,727,217 B2 | 6/2010 | Hancock-Cooke | |
| 8,764,722 B2 | 7/2014 | Rhein et al. | |
| 2014/0018756 A1* | 1/2014 | De Bruin .............. | A61F 13/505 604/385.01 |
| 2014/0350504 A1* | 11/2014 | Popp ................... | A61F 13/4942 604/385.28 |
| 2016/0262957 A1 | 9/2016 | Bishop et al. | |
| 2016/0270978 A1 | 9/2016 | Raycheck et al. | |
| 2018/0104116 A1 | 4/2018 | Bishop et al. | |
| 2019/0083331 A1 | 3/2019 | Barnes | |

FOREIGN PATENT DOCUMENTS

| | | |
|---|---|---|
| CN | 211244103 | 8/2020 |
| EP | 3482729 A1 | 5/2019 |
| EP | 3482730 A1 | 5/2019 |
| WO | WO2018124993 A1 | 7/2018 |

OTHER PUBLICATIONS

International Search Report and Written Opinion for PCT/US2020/038733 dated Feb. 11, 2020, 9 pages.
The Bump, Best Disposable Diapers, Retrieved from https://www.thebump.com/a/best-disposable-diapers, 2019, 17 Pages.

* cited by examiner

*Primary Examiner* — Jacqueline F Stephens
(74) *Attorney, Agent, or Firm* — Dority & Manning, P.A.

(57) ABSTRACT

An absorbent article is disclosed that has various leak-proof features. The absorbent article, for instance, includes containment flaps that hold body exudates within the garment. The containment flaps are attached to the absorbent article by a plurality of bond lines at each end of the containment flaps. In order to restrict fluids from flowing between the bond lines, the containment flaps are further bonded at each end by a transverse bond pattern. In one embodiment, the transverse bond pattern can be formed from ultrasonic point bonds. The transverse bond patterns not only restrict leaks but also is aesthetically pleasing.

20 Claims, 7 Drawing Sheets

ABSORBENT ARTICLE WITH LEAK-PROOF CONTAINMENT FLAPS

RELATED APPLICATIONS

The present application is the National Stage entry of International Patent Application No. PCT/US2020/038733, published as WO 2021/257095, which is incorporated herein by reference in its entirety.

BACKGROUND

Personal care absorbent articles such as diapers, training pants, adult incontinence garments, absorbent swim wear, feminine hygiene articles and the like, typically include a liquid-permeable bodyside liner, a liquid-impermeable outer cover, and an absorbent structure between the bodyside liner and the outer cover.

The absorbent structure, which is typically formed separately from the other layers, receives and retains aqueous liquid such as urine, menses, bowel movements, and the like which are exuded by the wearer. Absorbent structures are commonly formed of superabsorbent particles and hydrophilic absorbent fibers (e.g., cellulose), which are loosely mixed and entangled together to form an absorbent batt. Thermoplastic polymer fibers are sometimes included to provide reinforcement.

Absorbent articles as described above are designed to prevent fluids from leaking out of the article when being worn. The leaking of fluids should be prevented no matter whether the user is standing, sitting upright, or in a horizontal position. In this regard, problems have been experienced in the past in fluids leaking from the absorbent article when the user is laying down or sleeping. Although absorbent articles are well suited for retaining fluids when the user is upright, particular problems are experienced when the user is horizontally oriented. For example, fluids can find flow channels within the garment that cause fluids to leak around the waist region. These problems are especially prevalent when the user is a "side sleeper".

In view of the above, a need currently exists for an improved absorbent article that restricts leaking when the user is laying down or in an inclined position.

SUMMARY

In general, the present disclosure is directed to absorbent articles having improved leak-proof features. More particularly, the present disclosure is directed to absorbent articles that restrict fluids from leaking from the articles, especially when users of the articles are in a horizontal position, such as when reclining or sleeping. More particularly, the present disclosure is directed to bond patterns that are incorporated into the article that can be not only aesthetically pleasing but can block fluid passageways that can be present in the article and of concern when the articles are being worn while sleeping.

In one embodiment, for example, the present disclosure is directed to an absorbent article comprising an absorbent assembly. The absorbent assembly includes a liquid impermeable outer cover, a liquid permeable bodyside liner, and an absorbent body disposed between the outer cover and the bodyside liner. The absorbent assembly includes a front waist region, a rear waist region, and a crotch region extending between the front waist region and the rear waist region. The absorbent assembly further includes a body facing surface opposite an outer cover surface.

The absorbent article further includes a first containment flap extending between the front waist region and the rear waist region and a second containment flap extending between the front waist region and the rear waist region. Each of the containment flaps comprise a base portion coupled to the body facing surface and a projection portion configured to extend away from the body facing surface. Each containment flap includes a first end positioned adjacent the front waist region and a second and opposite end positioned adjacent the back waist region. The second end of the first containment flap is attached to the body facing surface by a bond area that may include a plurality of vertical bond lines that extend in a first direction. In addition to vertical bond lines, the bond area can have any suitable bond pattern and is generally formed through adhesive bonds. The bond area, however, is not continuous and includes various passageways that allow for fluid flow. For instance, the vertical bond lines can extend in a longitudinal or length direction. These bond lines can be spaced apart and thus form tunnels or passageways that allow fluid flow, especially when the absorbent article is in a horizontal position.

Similarly, the second end of the second containment flap can be attached to the body facing surface by a bond area, such as a plurality of bond lines that extend in the first direction.

In accordance with the present disclosure, the absorbent article further includes a first transverse bond pattern that intersects or is positioned adjacent to the bond area positioned at the second end of the first containment flap and a second transverse bond pattern that intersects or is positioned adjacent to the bond area positioned at the second end of the second containment flap. The first transverse bond pattern and the second transverse bond pattern restrict fluids from flowing through the bond areas that attach the ends of the containment flaps to the body facing surface.

In one embodiment, the first end of the first containment flap and the first end of the second containment flap can also include similar bond patterns. For instance, the first end of the first containment flap can be attached to the body facing surface by a bond area. A third transverse bond pattern can intersect the bond area at the first end of the first containment flap. Similarly, the first end of the second containment flap can be attached to the body facing surface by a bond area, such as a plurality of vertical bond lines that extend in the first direction. The absorbent article can include a fourth transverse bond pattern that intersects the plurality of vertical bond lines positioned at the first end of the second containment flap. In one embodiment, the absorbent article can include third and fourth transverse bond patterns as described above without including the first and second transverse bond patterns.

In one aspect, the bond areas that attach the ends of the containment flaps to the body facing surface can be adhesive bond lines while the transverse bond patterns can be formed from pressure bonds, ultrasonic bonds or thermal bonds. For example, the transverse bond patterns can comprise a pattern of point bonds. The point bonds can have a largest dimension (e.g. length, width, diameter, etc.) of from about 0.5 mm to about 4 mm, such as from about 0.75 mm to about 3 mm. The transverse bond patterns can have any suitable shape. For instance, the transverse bond patterns can be linear or curved. In one embodiment, the transverse bond patterns can have an arc-like shape. For example, the transverse bond patterns can include a convex surface opposite a concave surface. The convex surface can face the crotch region of the absorbent article. In one aspect, each transverse bond pattern can comprise two adjacent columns of point bonds that extend over a respective containment flap.

In one aspect, the transverse bond patterns can be skew to the bond areas or to the length direction on the respective containment flap. In one embodiment, the transverse bond pattern is perpendicular to the bond areas. The transverse bond pattern can extend over the entire width of the respective containment flap or can only extend over only a portion of the width of the respective containment flap. The transverse bond pattern can also extend beyond the containment flap and onto the body facing surface. In one embodiment, each transverse bond pattern can extend across a corner of a corresponding containment flap.

In one embodiment, the containment flap contains a plurality of elastic strips. The transverse bond pattern can intersect the plurality of vertical bond lines without intersecting the elastic strips or portions of the plurality of elastic strips. In one aspect, the transverse bond patterns are applied and the elastic strips are then retracted where there is no overlap. In this embodiment, the transverse bond patterns do no intersect a longitudinally extending line coincident with at least some of the elastic strands that extend between the front and rear waste regions of the absorbent article.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
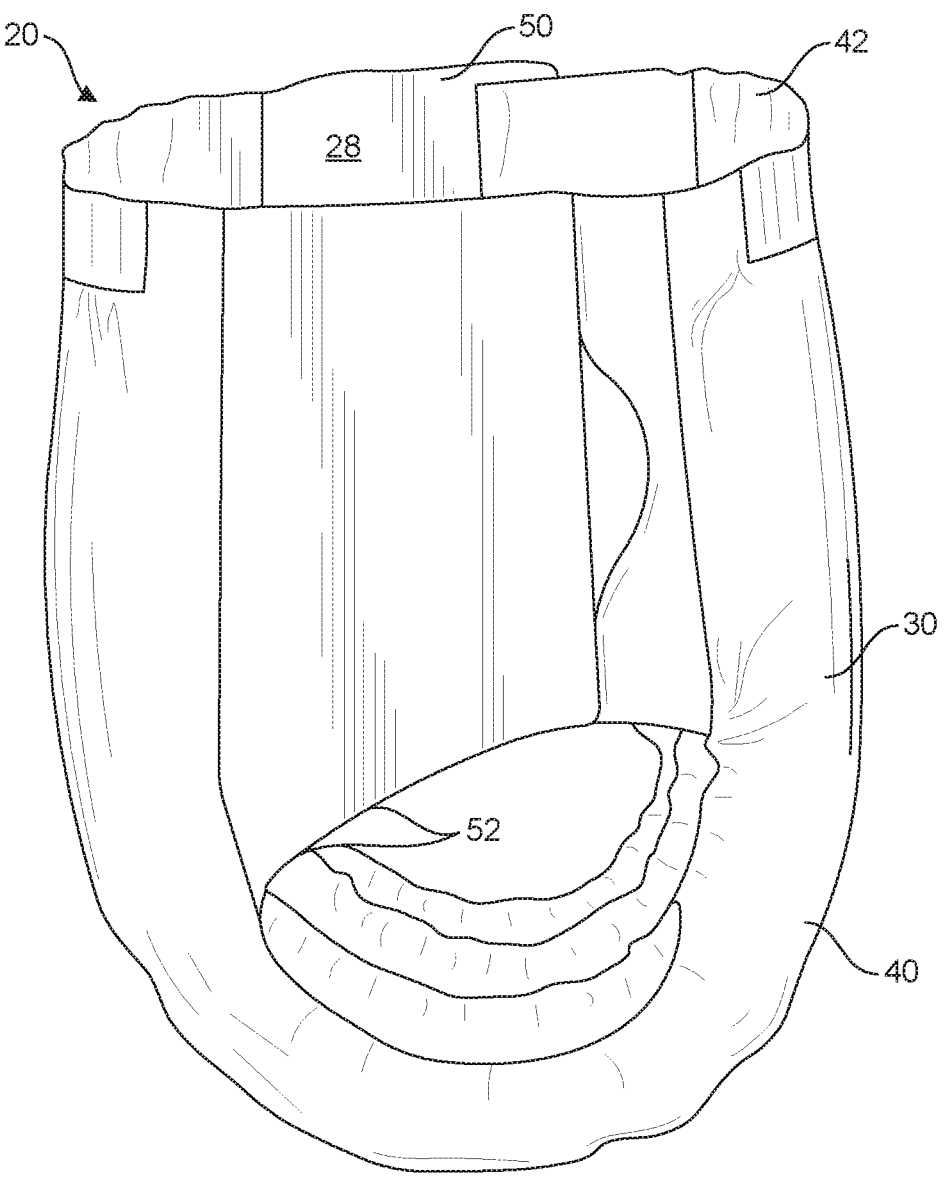
FIG. 1 is a side perspective view of one embodiment of an absorbent article that may be made in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to absorbent articles that are well suited to preventing fluid leaks. More particularly, absorbent articles designed in accordance with the present disclosure have unique bonding patterns that restrict fluids from escaping from the absorbent article through the waist opening when the wearer is in a horizontal position, such as when the wearer is sleeping. As will be explained in greater detail below, a decorative and aesthetic-pleasing bond pattern can be applied to the absorbent article at strategic locations where fluid flow may otherwise occur.

Referring now to the drawings and in particular to FIG. 1, one suitable embodiment of an absorbent article is illustrated in the form of a child's toilet training pant and is indicated generally in its entirety by the reference numeral 20. The term absorbent article generally refers to articles that may be placed against or in proximity to a body of a wearer to absorb and/or retain various exudates from the body. The absorbent training pant 20 may or may not be disposable. "Disposable" refers to articles that are intended to be discarded after a limited period of use instead of being laundered or otherwise conditioned for reuse. It is understood that the embodiments of the present disclosure are suitable for use with various other absorbent articles intended for personal wear, including but not limited to diapers, swim diapers, feminine hygiene products (e.g., sanitary napkins), incontinence products, medical garments, surgical pads and bandages, other personal care or health care garments, and the like without departing from the scope of the present disclosure.

Figure 2:
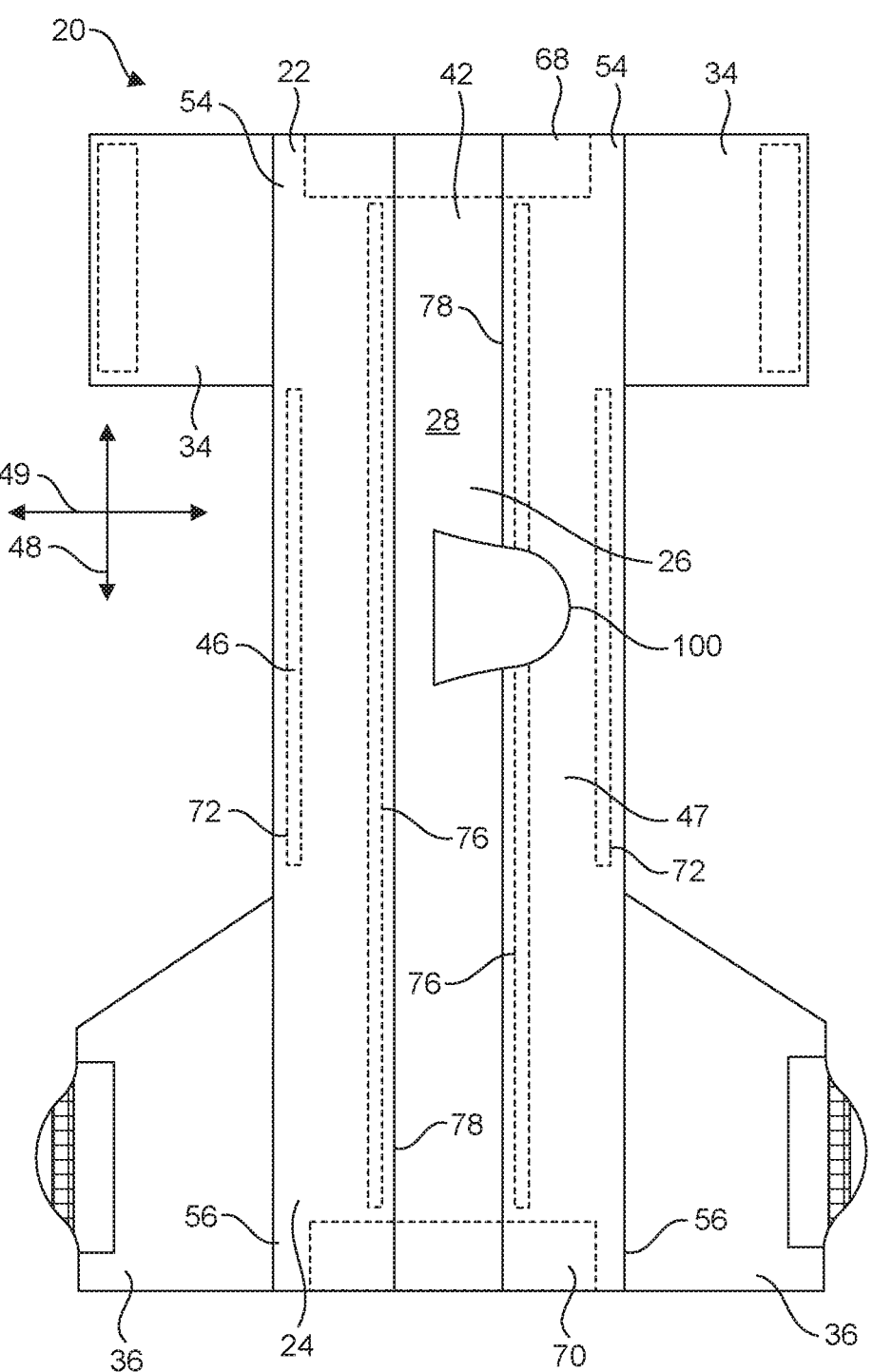
FIG. 2 is a top plan view of the absorbent article illustrated in FIG. 1 with the absorbent article in an unfolded and laid flat condition, and showing a body facing surface of the absorbent article adapted to face the wearer during use.

The training pant 20 is illustrated in FIG. 1 in a fully assembled (i.e., as assembled during initial manufacture) configuration (broadly referred to herein as a wear configuration of the pant) having a waist opening 50 and a pair of leg openings 52. The training pant 20 includes an inner surface or body facing surface 28 configured for contiguous relationship with the wearer, and an outer surface 30 opposite the inner surface. With additional reference to FIG. 2, the training pant includes an absorbent assembly containing an outer cover 40, a bodyside liner 42 opposite the outer cover 40, and an absorbent structure 100 disposed between the outer cover 40 and the bodyside liner 42. Arrows 48 and 49 in FIG. 2 depict the orientation of a longitudinal axis and a transverse or lateral axis, respectively, of the training pant 20.

The bodyside liner 42 is connected to the outer cover 40 in a superposed relation by suitable means such as adhesives, ultrasonic bonds, thermal bonds, pressure bonds, or combinations thereof.

The outer cover 40 suitably comprises a material which is substantially liquid impermeable. The outer cover 40 can be a single layer of liquid impermeable material, but more suitably comprises a multi-layered laminate structure in which at least one of the layers is liquid impermeable. For instance, the outer cover 40 can include a liquid permeable outer layer and a liquid impermeable inner layer that are suitably joined together by an adhesive, ultrasonic bonding, thermal bonding, pressure bonding, or combinations thereof.

Suitable adhesives can be applied continuously or intermittently as beads, a spray, parallel swirls, or the like. The liquid permeable outer layer can be any suitable material, including materials that provide a generally cloth-like texture. The outer layer may also be made of those materials of which the liquid permeable bodyside liner 42 is made. While it is not a necessity for the outer layer to be liquid permeable, it is suitable that it provides a relatively cloth-like texture to the wearer.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver.

If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. One suitable "breathable" material is composed of a microporous polymer film or a nonwoven fabric that has been coated or otherwise treated to impart a desired level of liquid impermeability.

It is also contemplated that the outer cover 40 may be stretchable, and more suitably elastic. In particular, the outer cover 40 is suitably stretchable and more suitably elastic in at least the transverse, or circumferential direction of the pant 20. In other embodiments the outer cover 40 may be stretchable, and more suitably elastic, in both the transverse and the longitudinal direction.

The liquid permeable bodyside liner 42 is illustrated as overlying the outer cover 40 and absorbent structure 100, and may, but need not, have the same dimensions as the outer cover 40. The bodyside liner 42 is suitably compliant, soft feeling, and non-irritating to the wearer's skin. The bodyside liner 42 is also sufficiently liquid permeable to permit liquid body exudates to readily penetrate through its thickness to the absorbent structure 100. Further, the bodyside liner 42 can be less hydrophilic than the absorbent structure 100 to present a relatively dry surface to the wearer and permit liquid to readily penetrate through its thickness. The hydrophilic/hydrophobic properties can be varied across the length, width and/or depth of the bodyside liner 42 and absorbent structure 100 to achieve the desired wetness sensation or leakage performance.

The bodyside liner 42 can be manufactured from a wide selection of web materials, such as porous foams, reticulated foams, apertured plastic films, woven and non-woven webs, or a combination of any such materials. For example, the bodyside liner 42 may comprise a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

The bodyside liner 42 may also be stretchable, and, more suitably, it may be elastomeric. In particular, the bodyside liner 42 is suitably stretchable and more suitably elastomeric in at least the transverse 49, or circumferential direction of the pant 20. In other embodiments the bodyside liner 42 may be stretchable, and more suitably elastomeric, in both the transverse 49 and the longitudinal 48 directions.

Suitable elastomeric materials for construction of the bodyside liner 42 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon of Cleveland, Ohio), or PEBAX elastomers. The bodyside liner 42 can also be made from extensible materials as are described in U.S. patent application Ser. No. 09/563,417 filed on May 3, 2000 by Roessler et al. or from biaxially stretchable materials as are described in U.S. patent application Ser. No. 09/698,512 filed on Oct. 27, 2000 by Vukos et al., both of which are hereby incorporated by reference.

The absorbent structure 100 is suitably compressible, conformable, non-irritating to a wearer's skin, and capable of absorbing and retaining liquids and certain body wastes. The absorbent structure 100 may be formed from a variety of suitable materials. In one suitable embodiment, the absorbent structure 100 is formed from a suitably resilient, compressible material.

The absorbent structure 100 may include multiple layers in a Z-direction (e.g., thickness) of the absorbent structure 100. Such multiple layers may take advantage of differences in absorbent capacity, such as by placing a lower absorbent capacity layer closer to the bodyside liner 42 and a higher absorbent capacity layer closer to the outer cover 40.

The absorbent structure 100 may include absorbent materials, such as cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and preferably is capable of absorbing more than about 25 times its weight in liquid. Suitable superabsorbent materials are readily available from various suppliers. For example, Hysorb T 9700 superabsorbent, which is commercially available from BASF of Ludwigshafen, Germany, or Favor SXM 5600 superabsorbent, which is commercially available from Evonik of Essen, Germany.

The absorbent structure 100 of the illustrated embodiment is generally rectangular, although the absorbent structure 100 can have any suitable shape and size that enables the absorbent structure 100 to function as described herein.

The absorbent article 20 as shown in FIG. 2 can also include front side panels 34 and back side panels 36. The front side panels 34 and the back side panels 36 connect together to form the sides of the absorbent article 20 and help define the leg openings 52. In one aspect, the front side panels 34 can be integral with the back side panels 36. Alternatively, the front side panels 34 can be bonded to the back side panels 36. In still another aspect, the front side panels 34 can be refastenable with the back side panels 36. For example, hook and loop type fasteners can be used such that a front side panel 34 can be attached, disconnected, and reattached to a corresponding back side panel 36.

To enhance containment and/or absorption of body exudates, the absorbent article or training pant 20 may include a front waist elastic member 68, a rear waist elastic member 70, and leg elastic members 72 as shown in FIG. 2. The waist elastic members 68 and 70 can be operatively joined to the outer cover 40 and/or the bodyside liner 42 along opposite waist edges. The leg elastic members 72 can be operatively joined to the outer cover 40 and/or the bodyside liner 42 along opposite side edges of the chassis and positioned in a crotch region 26. The crotch region 26 is positioned inbetween a front waist region 22 and a back waist region 24.

The waist elastic members 68, 70 and the leg elastic members 72 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 72 include a plurality of dry-spun coalesced multifilament spandex elastomeric threads sold under the trade name LYCRA™ and available from E.I. DuPont de Nemours and Company, Wilmington, Del., U.S.A.

To enhance containment and/or absorption of any body exudates discharged from the wearer, the chassis or absorbent article 20 may include a pair of containment flaps 46 and 47 which are configured to provide a barrier to the transverse flow of body exudates. A flap elastic member 76, which may comprise a plurality of elastic strands, may be operatively joined with each containment flap 46 and 47 in any suitable manner. The elasticized containment flaps 46 and 47 define an unattached edge 78 which assumes an upright, generally perpendicular configuration in at least the crotch region 26 of the training pant 20 to form a seal against the wearer's body. The containment flaps 46 and 47 can be located along the leg openings, encircling at least a portion of each of the leg openings. Each containment flap 46 and 47 includes a base portion coupled to the body facing surface 28 along a seam and a projection portion configured to extend away from the body facing surface 28 and terminate at the unattached edge 78.

Each containment flap 46 and 47 includes a first end 54 positioned adjacent to the front waist region 22 and a second end 56 positioned adjacent to the back waist region 24. The first end 54 of each containment flap 46, 47 and the second end 56 of each containment flap 46, 47 are attached to the body facing surface 28. For example, in one embodiment, each end 54 and 56 of the containment flaps 46, 47 are attached to the bodyside liner 42.

Figure 3:
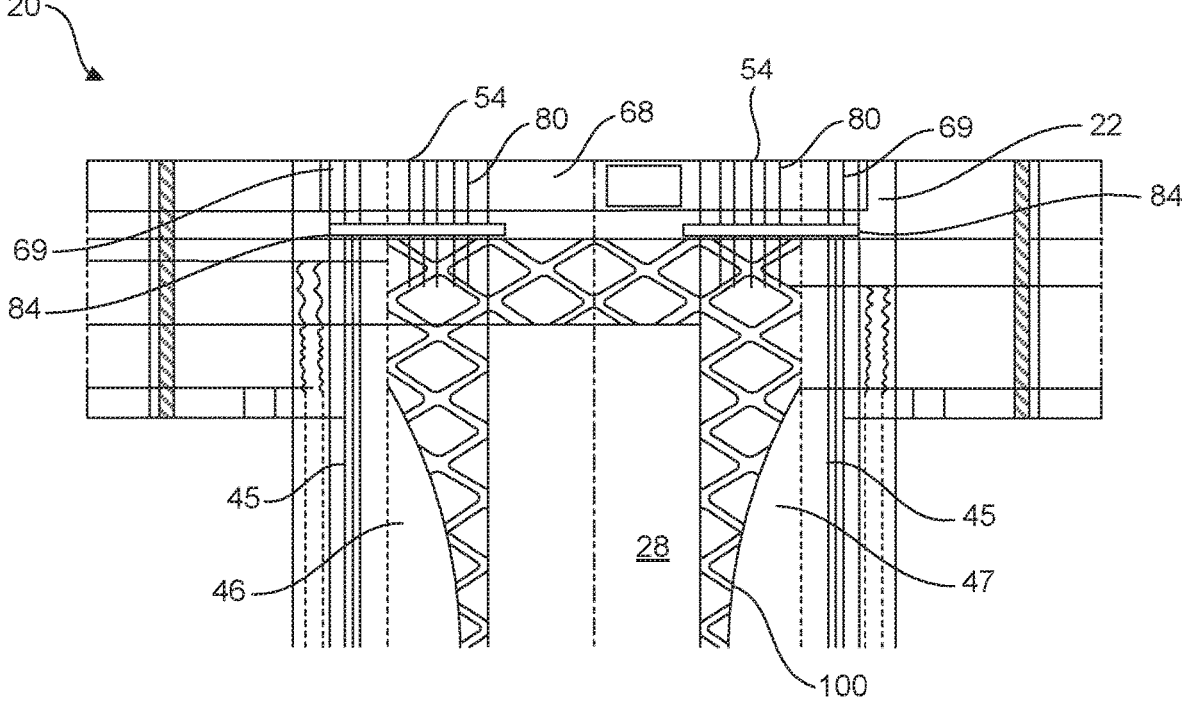
FIG. 3 is a partial top plan view of an absorbent article in an unfolded and laid flat condition showing one embodiment of a transverse bond pattern in accordance with the present disclosure.

Referring to FIG. 3, the attachment of the containment flaps 46 and 47 to the body facing surface 28 is shown in greater detail. FIG. 3 illustrates a portion of the absorbent article 20 shown in FIG. 2. FIG. 3 illustrates the front waist region 22 of the absorbent article 20. As shown in FIG. 3, a bond area including a plurality of bond members, such as bond lines 80 are used to attach the first end 54 of each containment flap 46 and 47 to the body facing surface 28. The plurality of bond lines 80 are generally in a parallel relationship and extend in the longitudinal direction 48. In this manner, the containment flaps 46 and 47 can be very quickly bonded to the body facing surface 28 of the absorbent article 20 during manufacture as the article is moving rapidly in the longitudinal direction or machine direction. The plurality of bond lines 80 have been found to form a very secure attachment of the containment flaps 46 and 47 to the absorbent article 20 while providing optimized functionality. The bond lines 80, for instance, have been found to allow for the use of thinner flap materials as the bond lines are less prone to adhesive bleed through.

Although the bond areas including the bond lines 80 can be incorporated into the absorbent article 20 very quickly and can secure both ends of the containment flaps of the body facing surface 28, the bond lines 80 can form channels or tunnels within the absorbent article 20. On occasion, fluid can flow through these channels and leak through the waist opening of the absorbent article 20. For instance, when a user of the absorbent article 20 is laying down, especially on his or her side, fluids can travel through the channels created by the bond lines 80. In addition to bond lines, the bond areas can also be formed from various other patterns of bond members, including spray patterns. In each of these embodiments, however, the bond areas may still allow for fluid flow, especially when the absorbent article is oriented horizontally.

In accordance with the present disclosure, the absorbent article 20 further includes transverse bond patterns 84. As shown in FIG. 3, the transverse bond patterns 84 can be positioned adjacent to or intersect the parallel bond lines 80 at the first end 54 of the containment flaps 46 and 47. The transverse bond patterns 84 are positioned so as to restrict fluids from flowing between the bond lines 80.

In FIG. 3, the transverse bond patterns 84 are positioned at the first end 54 of the containment flaps 46 and 47. Similar parallel bond lines 80 and transverse bond patterns 84 can also be positioned at the second end 56 of the containment flaps 46 and 47 in a similar arrangement. The position and amount of transverse bond patterns incorporated into the absorbent article 20 can depend upon the particular application. For instance, transverse bond patterns 84 can appear only at the first end 54 of the containment flaps 46 and 47, can be positioned only at the second end 56 of the containment flaps 46 and 47, or can be positioned at both ends 54 and 56 of the containment flaps 46 and 47.

In the embodiment illustrated in FIG. 3, the transverse bond patterns 84 are linear bond lines that extend generally perpendicular to the longitudinal direction 49. In the embodiment illustrated in FIG. 3, the transverse bond patterns 84 extend over the entire width of the containment flaps 46 and 47 and form a continuous bond from one end to an opposite end. The transverse bond patterns 84 as shown in FIG. 3, for instance, can extend onto the body facing surface 28 and over a seam 45 formed between the containment flaps 46 and 47 and the body facing surface 28. As shown in FIG. 3, the waist elastic member 68 also intersects the bond areas 80 and is attached to the article by waist elastic bond members 69. In addition to extending beyond the seam formed by the containment flaps 46 and 47, the transverse bond pattern 84 can also extend beyond the waist elastic bond member 69.

The transverse bond patterns 84 can comprise any suitable bonds. For instance, the transverse bond patterns 84 can be formed through adhesive bonding, through pressure bonding, through ultrasonic bonding, or through thermal bonding. In one aspect, the transverse bond patterns are formed through ultrasonic bonding. For instance, ultrasonic bonding rollers can be positioned along the manufacturing line that can quickly form ultrasonic bonds in the transverse direction as the absorbent article is being constructed along the machine direction.

In one aspect, the transverse bond patterns 84 can be formed through pressure bonding, such as through the use of rotary pressure bonding devices. One embodiment of pressure bonding, for example, is described in WO 2010/068150, which is incorporated herein by reference. During pressure bonding, for instance, the materials can be fed through a nip region between at least one cooperating pair of rotatable bonding rollers at ambient temperature to produce a bond pattern. For instance, the pressure bonding device can include at least one cooperating pair of counter-rotatable or counter-rotating bonding rollers. The bonding rollers can include at least one rotatable pattern roller and at least one rotatable anvil roller. The rollers can provide a distinctively high deformation rate or strain rate (length per length, per unit time) during a high-speed compression of the materials. The compressive mechanical deformation can induce internal heating of the materials and cause a temperature increase within the deformed materials. At the same time, thermal conduction can transfer heat away from the deformed materials. By controlling various different parameters, sufficient bonding can occur between the materials without having to heat the materials. During pressure bonding, lineal-pressure values can be from about $0.05\times10^6$ N/m to about $10\times10^6$ N/m, as an example. The lineal-pressure, however, is dependent upon various factors including the materials used.

The transverse bond patterns 84 incorporated into the absorbent article 20 can change and vary depending upon numerous factors. For instance, in alternative embodiments, the transverse bond patterns 84 may only extend over a portion of the width of the containment flaps 46 and 47. In one embodiment, the transverse bond patterns may extend over a portion of the containment flaps 46 and 47 and extend into the body facing surface 28 such as onto the bodyside liner 42.

In one aspect, the transverse bond patterns 84 extend over a portion of a corresponding containment flap 46, 47 without intersecting all or a portion of the flap elastic member 76. Intersecting the flap elastic member 76, for instance, may interfere with the flap elastics in some applications. In one embodiment, the flap elastic member 76 comprises a plurality of elastic strands. The transverse bond patterns 84 are applied to the absorbent article 20 so as to not intersect with all of the elastic strands or so as not to intersect with a portion of the elastic strands that make up the flap elastic member 76. In one aspect, the transverse bond patterns are applied and the elastic strips are then retracted where there is no overlap. In this embodiment, the transverse bond patterns do no intersect a longitudinally extending line coincident with at least some of the elastic strands that extend between the front and rear waste regions of the absorbent article.

In the embodiment illustrated in FIG. 3, the transverse bond patterns are linear and extend in the lateral direction 49. Alternatively, the transverse bond patterns 84 can have a skew relationship with the parallel bond lines 80. For instance, the transverse bond patterns 84 can be diagonal to the plurality of bond lines 80. In one aspect, the transverse bond patterns 84 may extend over a corner of a corresponding containment flap 46, 47.

In one embodiment, the transverse bond patterns 84 have an aesthetically pleasing appearance that can symbolize greater softness or other beneficial properties. For instance, the transverse bond patterns can be made with a decorative pattern.

Figure 4:
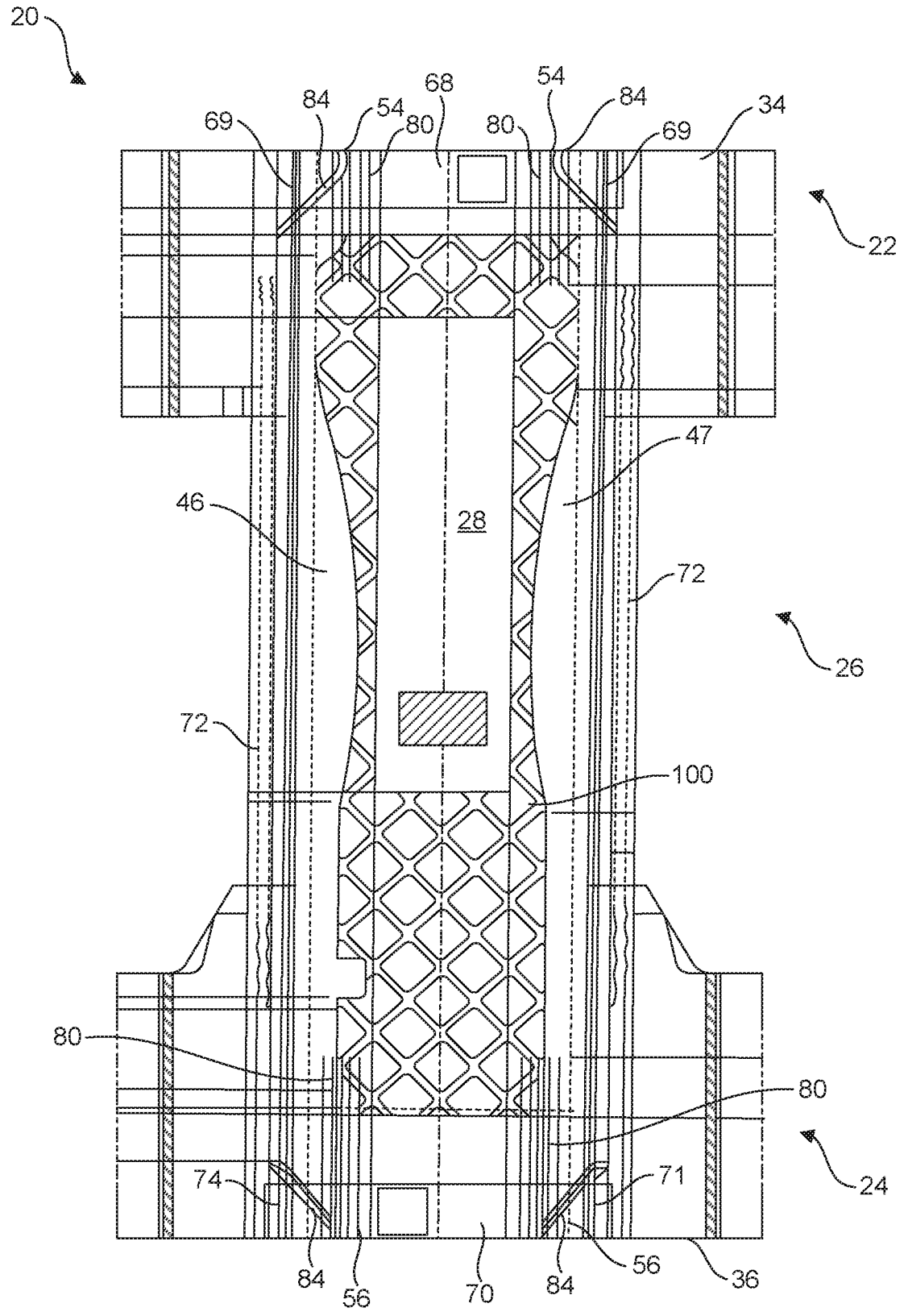
FIG. 4 is a plan view of one embodiment of an absorbent article including a pair of transverse bond patterns in accordance with the present disclosure.
Figure 5:
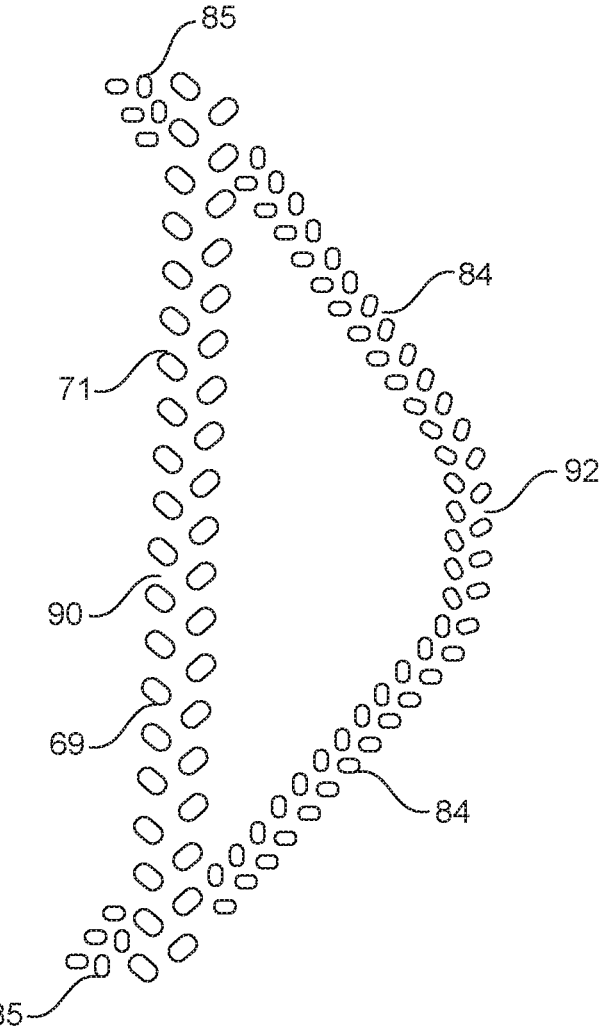
FIG. 5 is a plan view of one embodiment of a bond pattern that can be incorporated into the absorbent article as shown in FIG. 4.
Figure 6:
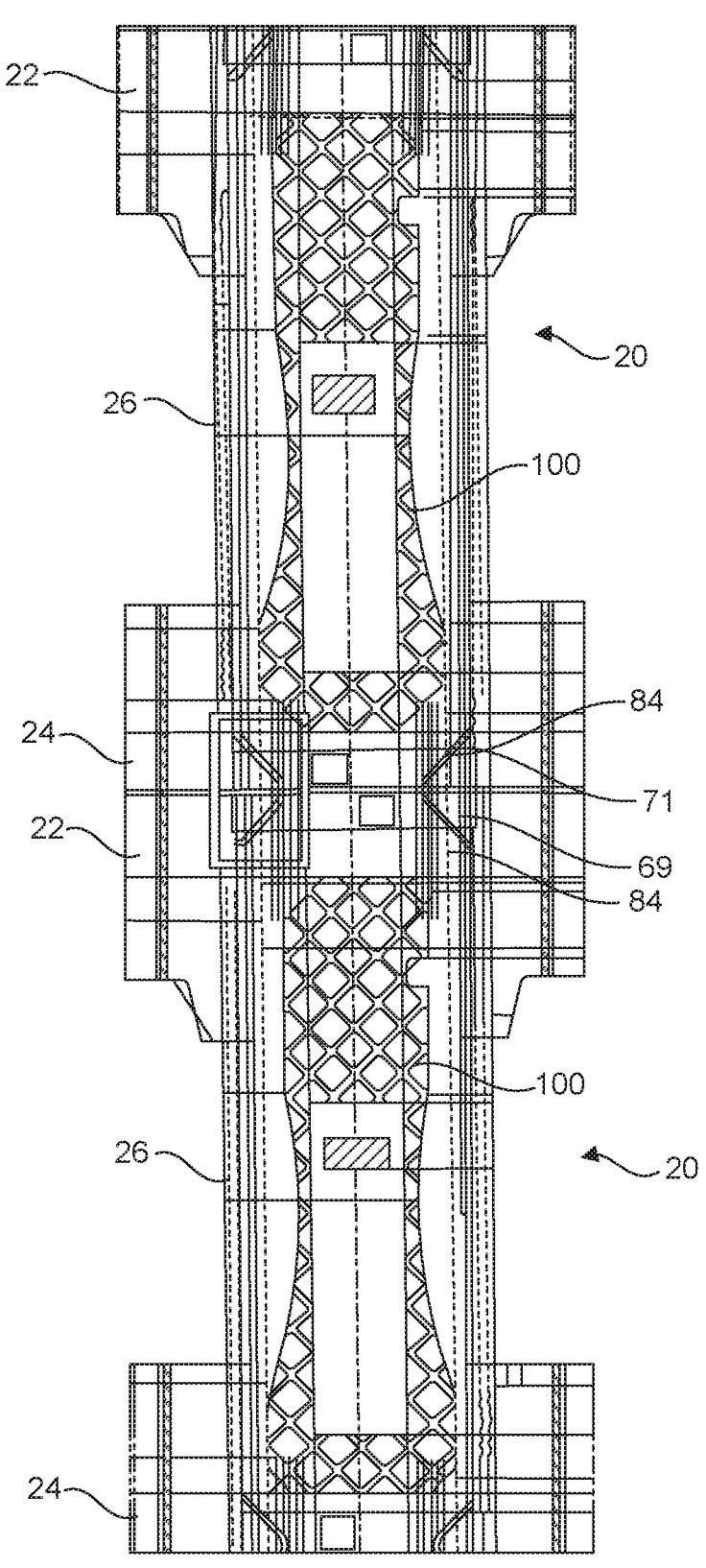
FIG. 6 is a plan view of absorbent articles during manufacture that illustrate use of the bond pattern shown in FIG. 5.

Referring to FIGS. 4-6, another embodiment of an absorbent article 20 made in accordance with the present disclosure is shown. Like reference numerals have been used to indicate similar elements. Referring to FIG. 4, the absorbent article includes a front waist region 22, a back waist region 24, and a crotch region 26 positioned between the front waist region 22 and the back waist region 24. The absorbent article 20 further includes front side panels 34 and back side panels 36. An absorbent structure 100 is positioned within the center of the article and extends from the front waist region 22 to the back waist region 24. The absorbent article 20 further includes a first containment flap 46 and a second containment flap 47 that both extend the length of the article. Each containment flap includes a first end 54 that is attached to a body facing surface 28 by a bond area 80 formed from, in this embodiment, a plurality of parallel bond lines. Similarly, each containment flap 46 and 47 includes a second end 56 that is also attached to the body facing surface 28 by bond areas 80.

The absorbent article 20 further includes a waist elastic member 68 positioned at the front waist region 22 and a waist elastic member 70 positioned at the back waist region 24. The waist elastic member 68 is attached to the article by waist elastic bond members 69. The waist elastic member 70, on the other hand, is attached to the absorbent article by waist elastic bond members 71.

In accordance with the present disclosure, the absorbent article 20 further includes transverse bond patterns 84 positioned in the front waist region 22 and transverse bond patterns 84 positioned at the back waist region 24. In this embodiment, the transverse bond patterns 84 have a curved shape and intersect corresponding bond areas 80. In addition, the transverse bond patterns 84 also intersect corresponding waist elastic bond members 69 and 71.

As shown in FIG. 4, the transverse bond patterns 84, in this embodiment, do not extend over the entire width of the containment flaps 46 and 47. In addition, the transverse bond patterns 84 also do not extend over the entire bond areas 80 that attach the containment flaps 46 and 47 to the body facing surface 28. As stated above, in other embodiments, the transverse bond pattern 84 may extend over the entire width of the containment flaps 46 and 47 and the entire width of the bond areas 80. The extent to which the transverse bond patterns extend over the containment flaps 46 and 47, however, can depend upon various factors. For example, as described above, the containment flaps 46 and 47 can include a flap elastic member 76 made from a plurality of elastic strands. In one aspect, the transverse bond patterns 84 may be incorporated into the absorbent article 20 without intersecting all of the elastic strands that make up the flap elastic member 76. In addition, the transverse bond patterns 84 can extend over the elastic flaps 46 and 47 and the bond areas 80 where fluid flow is problematic. In other areas, however, leakage may not be an issue and therefore may not require the presence of the transverse bond pattern 84.

In general, the transverse bond pattern can extend over a corresponding containment flap in an amount of from about 10% to about 100% of the width. For example, the transverse bond pattern can extend over greater than about 20%, such as greater than about 30%, such as greater than about 40%, such as greater than about 50%, such as greater than about 60%, such as greater than about 70%, such as greater than about 80% of the width of the containment flap and can extend generally less than about 100%, such as less than about 90%, such as less than about 80%, such as less than about 70%, such as less than about 60% of the width of a corresponding containment flap.

As shown in FIG. 4, the transverse bond patterns 84 extend over a portion of the containment flaps 46 and 47 and extend onto the body facing surface 28. For example, in one aspect, the transverse bond patterns 84 can extend over a seam formed between the containment flaps 46 and 47 and the body facing surface 28. In some applications, it is believed that this seam can also provide for fluid flow. In addition, as shown in FIG. 4, the transverse bond patterns 84 also extend beyond the waist elastic bond members 69 and 71.

Referring to FIG. 5, a bond pattern is illustrated that can be used to create not only the transverse bond patterns 84 as shown in FIG. 4, but also the waist elastic bond members 69 and 71. For example, as shown in FIG. 6, the bond pattern illustrated in FIG. 5 can be applied to the absorbent articles during manufacture and can extend over the front waist region 22 and the back waist region 24 of two adjacent absorbent articles. Once the absorbent articles are cut and separated, the resulting pattern as shown in FIG. 4 is created.

Referring to FIG. 5, for instance, the bond pattern includes a straight member 90 that intersects a curved member 92. The straight member 90 is used to form the waist elastic bond members 69 and 71, while the curved member 92 is used to form the transverse bond patterns 84.

As shown in FIG. 5, the bond pattern is comprised of point bonds. For instance, the bond pattern can be formed from two adjacent columns of point bonds. In the embodiment illustrated in FIG. 5, the straight member 90 is formed from larger point bonds than the curved member 92.

Referring to FIG. 6, two absorbent articles 20 are shown during the manufacture of the articles. The articles are moving in a machine direction and are initially attached together. Each absorbent article 20 includes a crotch region 26 positioned inbetween the front waist region 22 and the back waist region 24. Extending along the length of each absorbent article is an absorbent structure 100. As shown where the two absorbent articles 20 intersect, the bond pattern illustrated in FIG. 5 is applied over both absorbent articles in order to form transverse bond patterns 84, waist elastic bond member 69 and waist elastic bond member 71. Tying together the multiple bond patterns creates significant processing efficiency, only requiring a single bond maker or bonding device. As shown, the waist elastic bond members 69 and 71 extend in the machine direction while the transverse bond patterns 84 are skew to the machine direction. The transverse bond patterns 84 can be skew to the machine direction in order to ensure constant rolling contact between a horn and anvil when creating ultrasonic bonds or between a bonding roller and an anvil when producing thermal bonds or pressure bonds. In addition, using point bonds as shown in FIG. 5 facilitates formation of the bond pattern when using one of the above bonding techniques.

Referring to FIG. 5, the bonding pattern includes the curved member 92 that intersects the straight member 90. As shown in FIG. 5, the curved member 92 includes an extension 85 at each end that extends beyond the straight member 90. When applied to an absorbent article, the bond pattern illustrated in FIG. 5 ensures that the transverse bond patterns 84 extend beyond the waist elastic bond members 69 and 71. The extensions 85 as shown in FIG. 5 have been found to further restrict fluid escape from the absorbent article, especially when the absorbent article is in a horizontal position.

Figure 7:
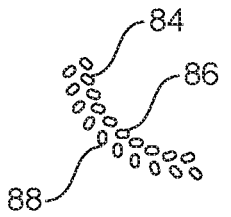
FIG. 7 is a plan view of one embodiment of a pair of transverse bond patterns in accordance with the present disclosure.
Figure 7:
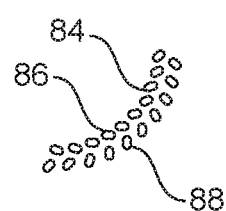

Referring now to FIGS. 7-10, more embodiments of transverse bond patterns 84 that may be used in accordance with the present disclosure are shown. For example, referring to FIG. 7, a pair of cooperating transverse bond patterns 84 are shown. The bond patterns 84 are designed to be positioned on opposite sides of the absorbent article 20 at the first end 54 or second end 56 of the containment flaps 46 and 47. The bond patterns 84 are mirror images of each other. As shown, the bond patterns 84 are comprised of point bonds. More particularly, each bond pattern 84 is comprised of two adjacent columns of point bonds. The bond patterns 84 form an arc-shaped pattern. For example, the bond patterns 84 include a concave portion 86 opposite a convex portion 88. When applied to an absorbent article, the convex portion 88 is intended to face the crotch region 26, while the concave portion 86 is configured to face the waist opening. Alternatively, the concave portion 86 can face the crotch region 26, while the convex portion 88 can be configured to face the waist opening. When applied to the containment flaps 46 and 47, the bond patterns 84 as shown in FIG. 7 are intended to intersect the parallel bond lines adjacent to a corner of the second end 56 of the containment flaps 46 and 47. These bond patterns 84 can be visible to a user when donning the product and can provide aesthetic appeal.

As described above, the bond patterns 84 as shown in FIG. 7 are formed from point bonds. These point bonds, for instance, can be formed through pressure bonding, ultrasonic bonding or thermal bonding. The shape and size of the point bonds can vary depending upon the particular application. In general, the point bonds can have a largest dimension (i.e. width, length, or diameter) of greater than about 0.25 mm, such as greater than about 0.5 mm, such as greater than about 1 mm, such as greater than about 1.5 mm, such as greater than about 2 mm, and generally less than about 4 mm, such as less than about 3.5 mm, such as less than about 3 mm, such as less than about 2.5 mm.

The use of point bonds as described above can provide various advantages and benefits. Point bonds, for instance, may facilitate application of the bond patterns to the different materials that make up the absorbent article. In addition, continuous bonds as opposed to point bonds can create weaknesses within the absorbent article and when under tension can have a "zippering" effect and delaminate. The spacing between the point bonds can depend upon numerous factors including the manner in which the point bonds are applied to the materials. In general, the spacing between the point bonds should be small enough and sufficient so as to restrict fluid flow in and around the point bonds.

As described above, in one embodiment, the bond patterns 84 are made through pressure bonding. In fact, the patterns illustrated in FIG. 5 and in FIGS. 7-10 are well suited for application to the absorbent article through pressure bonding. For instance, the patterns are constructed such that, during pressure bonding, pressure remains constant along the transverse access which allows for the creation of stronger and more uniform bonds. More particularly, the bond patterns can be designed such that the contact area during pressure bonding is uniform across the length of the article.

Figure 8:
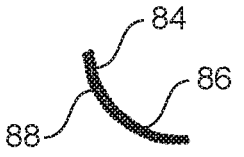
FIG. 8 is a plan view of one embodiment of a pair of transverse bond patterns in accordance with the present disclosure.
Figure 8:
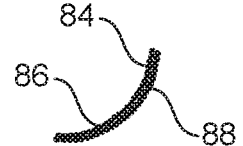
Figure 9:
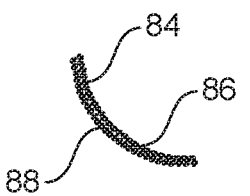
FIG. 9 is a plan view of one embodiment of a pair of transverse bond patterns in accordance with the present disclosure.
Figure 9:
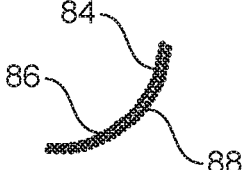

Referring to FIGS. 8 and 9, further embodiments of transverse bond patterns 84 in accordance with the present disclosure are shown. The transverse bond patterns 84 illustrated in FIGS. 8 and 9 are similar to the embodiment illustrated in FIG. 7. In FIGS. 8 and 9, however, the point bonds are smaller and can be spaced closer together. The transverse bond patterns 84 as shown in FIGS. 8 and 9 are to be positioned at the ends of the containment flaps 46 and 47 and are designed to intersect parallel bond lines for restricting fluids from flowing between the bond lines.

Figure 10:
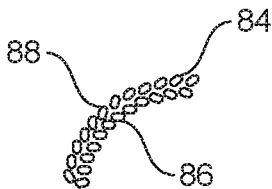
FIG. 10 is a plan view of one embodiment of a pair of transverse bond patterns in accordance with the present disclosure.
Figure 10:
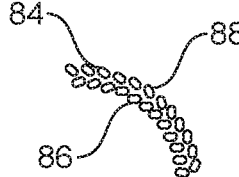

Referring to FIG. 10, still another embodiment of transverse bond patterns 84 made in accordance with the present disclosure are shown. In the embodiment illustrated in FIG. 10, the bond patterns 84 are mirror images of each other and are designed to be placed at the ends of the containment flaps 46 and 47. As shown, the bond patterns 84 include a concave portion 86 and a convex portion 88. The convex portion 88 is designed to face the crotch region 26 of the absorbent article 20.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An absorbent article comprising: an absorbent assembly comprising a liquid impermeable outer cover, a liquid permeable bodyside liner, and an absorbent body disposed between the outer cover and the bodyside liner, the absorbent assembly including a front waist region, a rear waist region, and a crotch region extending between the front waist region and the rear waist region, the absorbent assembly further including a body facing surface; a first containment flap extending between the front waist region and the rear waist region and a second containment flap extending between the front waist region and the rear waist region, each of the first containment flap and the second containment flap comprising a base portion coupled to the body facing surface and a projection portion configured to extend away from the body facing surface, each of the first containment flap and the second containment flap including a first end positioned adjacent the front waist region and a second and opposite end positioned adjacent the back waist region, the second end of the first containment flap being attached to the body facing surface by a bond area, the second end of the second containment flap also being attached to the body facing surface by a bond area; and a first transverse bond pattern that is positioned adjacent to or intersects the bond area at the second end of the first containment flap and a second transverse bond pattern that is positioned adjacent to or intersects the bond area at the second end of the second containment flap, wherein the first transverse bond pattern comprises a pattern of point bonds and the second transverse bond pattern comprises a pattern of point bonds, wherein the first containment flap has a length and a width and wherein the first transverse bond pattern extends across only a portion of the width of the first containment flap and wherein the second containment flap has a length and a width and wherein the second transverse bond pattern extends across only a portion of the width of the second containment flap, and wherein the first containment flap and the second containment flap include a flap elastic member, such that the first transverse bond pattern and the second transverse bond pattern do not intersect the flap elastic member of the first containment flap and the second containment flap.

2. The absorbent article as defined in claim 1, wherein the first transverse bond pattern and the second transverse bond pattern restrict fluids from flowing through the bond area at the second end of the first containment flap and/or the bond area at the second end of the second containment flap.

3. The absorbent article as defined in claim 1, wherein the first transverse bond pattern and the second transverse bond pattern comprise ultrasonic bonds, pressure bonds, or thermal bonds.

4. The absorbent article as defined in claim 1, wherein the bond areas at the second end of the first containment flap and/or the bond area at the second end of the second containment flap comprise a plurality of bond lines that extend in a first direction and wherein the first transverse bond pattern intersects the plurality of bond lines positioned at the second end of the first containment flap and the second transverse bond pattern intersects the plurality of bond lines positioned at the second end of the second containment flap.

5. The absorbent article as defined in claim 4, wherein the absorbent assembly includes a longitudinal direction that extends from the front waist region to the rear waist region and wherein the first direction is the longitudinal direction.

6. The absorbent article as defined in claim 4, wherein the first transverse bond pattern is skew to the bond lines that attach the first containment flap to the body facing surface and wherein the second transverse bond pattern is skew to the bond lines that attach the second containment flap to the body facing surface.

7. The absorbent article as defined in claim 1, wherein the first end of the first containment flap is attached to the body facing surface by a plurality of bond lines that extend in the first direction and the first end of the second containment flap is attached to the body facing surface by a plurality of bond lines that extend in the first direction and wherein the absorbent assembly further includes a third transverse bond pattern that intersects the plurality of bond lines positioned at the first end of the first containment flap and a fourth transverse bond pattern that intersects the plurality of bond lines positioned at the first end of the second containment flap.

8. The absorbent article as defined in claim 1, wherein the first transverse bond pattern is in the form of an arc-shaped pattern and wherein the second transverse bond pattern is in the shape of an arc-shaped pattern.

9. The absorbent article as defined in claim 8, wherein the first transverse bond pattern includes a concave portion and a convex portion, the convex portion facing the crotch region, the second transverse bond pattern including a concave portion and a convex portion, the convex portion facing the crotch region.

10. The absorbent article as defined in claim 1, wherein the first transverse bond pattern comprises two adjacent columns of point bonds and wherein the second transverse bond pattern comprises two adjacent columns of point bonds.

11. The absorbent article as defined in claim 1, wherein the first transverse bond pattern extends beyond a width of the first containment flap and wherein the second transverse bond pattern extends beyond a width of the second containment flap.

12. The absorbent article as defined in claim 1, wherein the back waist region includes a back waist elastic member, the back waist elastic member extending in a lateral direction and being attached to the absorbent article on each side of the back waist elastic member by a waist elastic bond member, and wherein the first transverse bond pattern and the second transverse bond pattern each intersect a corresponding waist elastic bond member.

13. The absorbent article as defined in claim 12, wherein the first transverse bond pattern and the waist elastic bond member are all part of a common overall bond pattern and wherein the second transverse bond pattern and a corresponding waist elastic bond member are both part of an overall common bond pattern.

14. The absorbent article as defined in claim 12, wherein the first transverse bond pattern, the second transverse bond pattern, and the waist elastic bond members all terminate along a waste edge of the absorbent article.

15. The absorbent article as defined in claim 1, wherein the first containment flap includes a plurality of elastic strands that extend along a length of the first containment flap, and wherein the first transverse bond pattern does not intersect with at least a portion of the elastic strands or with a portion of longitudinally extending lines coincident with the elastic strands that extend between the front waist region and the back waist region, and wherein the second containment flap includes a plurality of elastic strands that extend along a length of the second containment flap and wherein the second transverse bond pattern does not intersect with at least a portion of the elastic strands on the second containment flap or with a portion of longitudinally extending lines coincident with the elastic strands that extend between the front waist region and the back waist region.

16. The absorbent article as defined in claim 1, wherein the first transverse bond pattern extends over a corner of the second end of the first containment flap and the second transverse bond pattern extends over a corner of the second end of the second containment flap.

17. The absorbent article as defined in claim 1, wherein the point bonds have a largest dimension of from about 1 mm to about 4 mm.

18. The absorbent article as defined in claim 1, wherein the first transverse bond pattern bonds the first containment flap to the body facing surface and the second transverse bond pattern bonds the second containment flap to the body facing surface.

19. The absorbent article as defined in claim 1, wherein the first transverse bond pattern and the second transverse bond pattern form decorative patterns on the interior of the absorbent article.

20. An absorbent article comprising: an absorbent assembly comprising a liquid impermeable outer cover, a liquid permeable bodyside liner, and an absorbent body disposed between the outer cover and the bodyside liner, the absorbent assembly including a front waist region, a rear waist region, and a crotch region extending between the front waist region and the rear waist region, the absorbent assembly further including a body facing surface; a first containment flap extending between the front waist region and the rear waist region and a second containment flap extending between the front waist region and the rear waist region, each of the first containment flap and the second containment flap comprising a base portion coupled to the body facing surface and a projection portion configured to extend away from the body facing surface, each of the first containment flap and the second containment flap including a first end positioned adjacent the front waist region and a second and opposite end positioned adjacent the back waist region, the first end of the first containment flap being attached to the body facing surface by a plurality of bond lines that extend in a first direction, the first end of the second containment flap also being attached to the body facing surface by a plurality of bond lines that extend in the first direction; and a first transverse bond pattern that intersects the plurality of bond lines positioned at the first end of the first containment flap and a second transverse bond pattern that intersects the plurality of bond lines positioned at the first end of the second containment flap, wherein the first transverse bond pattern comprises a pattern of point bonds and the second transverse bond pattern comprises a pattern of point bonds wherein the first containment flap has a length and a width and wherein the first transverse bond pattern extends across only a portion of the width of the first containment flap and wherein the second containment flap has a length and a width and wherein the second transverse bond pattern extends across only a portion of the width of the second containment flap, and wherein the first containment flap and the second containment flap include a flap elastic member, such that the first transverse bond pattern and the second transverse bond pattern do not intersect the flap elastic member of the first containment flap and the second containment flap.

\* \* \* \* \*